United States Patent [19]

Johnson

[11] 4,113,756

[45] Sep. 12, 1978

[54] CONVERSION OF MONO-VALENT THALLIUM TO TRI-VALENT THALLIUM

[75] Inventor: Richard A. Johnson, Midland Park, N.J.

[73] Assignee: Halcon International, Inc., New York, N.Y.

[21] Appl. No.: 740,147

[22] Filed: Nov. 8, 1976

[51] Int. Cl.$^2$ ............................................. C07F 5/00
[52] U.S. Cl. .............................. 260/429 R; 423/395; 423/495; 423/544
[58] Field of Search .................. 260/429 R; 423/395, 423/495, 544

[56] References Cited

U.S. PATENT DOCUMENTS

| | | | |
|---|---|---|---|
| 3,399,956 | 9/1968 | Hirose et al. | 423/495 |
| 3,436,409 | 4/1969 | Hill et al. | 260/348.23 |
| 3,479,262 | 11/1969 | MacLean et al. | 204/80 |
| 3,594,395 | 7/1971 | Taylor et al. | 260/429 R |

FOREIGN PATENT DOCUMENTS

| | | | |
|---|---|---|---|
| 13,104 | 2/1974 | Japan | 260/429 R |
| 44,116 | 11/1976 | Japan | 260/429 R |

OTHER PUBLICATIONS

Spencer, L., Anorg. Chem. vol. 44 pp. 379–407 (1905).
Spiro et al., J. Chem. Soc. pp. 78–96 (1965).
Chemical Abstracts, 64 13800h (1966).
Chemical Abstracts, 67 96372e (1967).
Chemical Abstracts, 63 1471a (1965).
Chemical Abstracts, 73 47165e (1970).

*Primary Examiner*—Helen M. S. Sneed
*Attorney, Agent, or Firm*—William C. Long; David Dick; Riggs T. Stewart

[57] ABSTRACT

A mono-valent thallium compound is converted to a trivalent thallium compound by treating the thallium (I) compound with molecular oxygen in the presence of a Group VIII noble metal catalyst and in the presence of a promoter comprising an alkali metal compound to oxidize the thallium (I) compound to a thallium (III) compound.

11 Claims, No Drawings

CONVERSION OF MONO-VALENT THALLIUM TO TRI-VALENT THALLIUM

This invention relates to the oxidation of Thallium (I) to thallium (III).

Trivalent thallium compounds, i.e., thallic compounds, have been used as oxidizing agents in various reactions. For example, Kruse et al., J. Org. Chem. 36, 1154 (1971) describes the epoxidation of certain olefins with thallic acetate and Kruse U.S. Pat. No. 3,641,067 relates to the preparation of the epoxides of propylene and isobutylene by means of lower thallic alkanoates.

In all of these reactions the trivalent thallium is reduced to the monovalent state and if the thallium is to be reused in the reaction it is necessary to reoxidize or "regenerate" it by converting thallium (I) to thallium (III). Various methods for effecting this conversion have been proposed and are more or less effective. Thus, Hirose et al. U.S. Pat. No. 3,399,956 describes the oxidation of Tl(I) to Tl(III) by means of molecular oxygen in an acidic aqueous medium containing chloride or bromide ion and an ion of a redox metal such as copper, mercury, chromium, manganese, iron, cobalt, and nickel. Hirose et al. refer to earlier processes for effecting the conversion of Tl(I) to Tl(III) and point out the problems involved in achieving the desired oxidation and the disadvantages and drawbacks of prior procedures. While the Hirose et al. process is described as an improvement over processes previously proposed, it is limited to the use of aqueous chloride or bromide solutions so that the thallium (III) is always produced as a chloride or bromide and it is generally necessary to use the redox metal in large amounts in relation to the thallium compound being treated. It is proposed to convert thallium (I) to thallium (III) in the application of William Brill, entitled "Catalytic Conversion of Thallium (I) to Thallium (III)" by means of molecular oxygen using a Group VIII noble metal as a catalyst but conversions to thallium (III) are limited, said application field on even date herewith.

It is an object of this invention to provide a process for converting thallium (I) to thallium (III) which makes possible high conversions.

In accordance with the invention, a monovalent thallium compound is converted to a trivalent thallium compound by treating the thallium (I) compound with molecular oxygen in the presence of a Group VIII noble metal catalyst and in the presence of a promoter for the catalyst in a fluid medium to oxidize the thallium (I) compound to achieve high conversions to thallium (III) in a rapid and efficient manner.

The Group VIII noble metals comprise platinum, palladium, rhodium, ruthenium, osmium and iridium, but platinum, palladium, ruthenium and rhodium are preferred, especially platinum and palladium. Mixed catalysts can be used if desired. The catalyst is preferably used in a heterogenous system, e.g., in the form of a suspension in the reaction medium and in this case the catalyst is ordinarily supported upon a solid carrier. The Group VIII noble metal catalyst may be suitably added as a compound of the above-mentioned metals, e.g., an oxide, preferably on a carrier, but it is most preferred to add the catalyst as the finely-divided metal, e.g., platinum black, or as the metal supported on a carrier.

When the Group VIII noble metal catalyst is suported upon a carrier, the carrier or substrate which is employed is suitably in the form of a porous solid of such size that it can be readily dispersed in the liquid reaction medium, e.g., from 400 mesh/inch to ½-inch particle sizes. Such carrier materials are exemplified by pumice, alumina, silica, silica-alumina, magnesia, diatomaceous earth, bauxite, titania, zirconia, clays, both natural and acid treated such as Super-Filtrols, attapulgus clay (attapulgite), lime, magnesium silicate, silicon carbode, activated and unactivated carbons, zeolites as well as the zeolitic molecular sieves, solid forms, such as ceramic honeycombs, and porous organic polymers. The above carriers are suitably used in the form of regular and irregular particles such as tubes, balls, broken pieces, and the like. Such supported forms of the Group VIII noble metals and their compounds are prepared by conventional methods, e.g., deposition from a solution, for example as described in Schultz U.S. Pat. No. 3,717,670 in connection with rhodium compounds and, indeed, many such supported catalysts are available commercially, particularly in the case of the zero valent free metal.

Concentrations of the Group VIII noble metal component on the support can vary widely but illustrative concentrations lie within the range of 0.1 to 20 wt. %. Higher concentrations may, however, be used if desired.

The ratio of catalyst to monovalent thallium compound can also vary over a wide range. For example, 0.1 to 40 mols of catalyst per 100 mols of monovalent thallium compound are advantageously used, but lesser or greater amounts may be employed, if desired, the upper limit being determined only by economic considerations and the lower limit only by the amount which will be catalytically effective. In any case, only catalytic quantities are required to bring about a rapid conversion.

The promoter for the Group VIII noble metal catalyst in accordance with the invention is an alkali metal compound, i.e., a compound of a metal of Group IA of the Periodic Chart of the Elements. Preferred are compounds of sodium, potassium, rubidium and cesium. The compound is generally one that is soluble in the reaction mixture. Typical compounds are the oxides, hydroxides, salts, both organic and inorganic, such as the carboxylates, the carbonates, and the like. Preferably the compounds give a basic reaction. Most preferably the carboxylates are used and these may be alkyl carboxylates, including cycloalkyl carboxylates, or aryl carboxylates, e.g., acetates, propionates, butyrates, benzoates, and the like, preferably containing up to 20 carbon atoms in the organic moiety. Most preferably, the alkali metal compound has an anion corresponding to the anion of the thallium (I) being treated.

The amount of alkali metal promoter is not critical and ordinarily can vary from 0.01 to 50 moles per mole of thallium (I) compound, preferably 0.1–10 moles.

Ordinarily, the higher the reaction temperature, the greater the reaction rate. It is unnecessary, however, to employ high temperatures. Normally, the reaction temperature may range from 10° to about 200° C. Typically, temperatures of 60° to 160° C. are used, but higher or lower temperatures are operable. Excessively high temperatures, however, are not advantageous because they may eventually result in reaction between the thallium compounds and the solvent. Total pressure is not a specific parameter of the process and atmospheric or superatmospheric pressures may be employed but desirably oxygen partial pressures above the reaction mixture of at least 20 psi, preferably 200 to 2000 psi are provided and higher oxygen partial pressures, e.g., up to 10,000 psi can be used, if desired. It is generally desirable to stir the reaction medium, particularly when a heterogenous catalyst is employed, and this may be effected by mechanical agitation, shaking, and like means known to the art.

Any convenient monovalent thallium compound can be treated in accordance with the invention. Typically, the compound will be a salt which may be organic, such as a carboxylate of an alkyl, cycloalkyl or aryl carboxylic acid containing up to 20 carbon atoms, such as an acetate or benzoate, or inorganic, such as a nitrate, a sulfate, or a halide, but other compounds may be used, if desired. The thallous compound is suitably one which is at least partly soluble in the liquid medium employed. Preferably the anion is organic.

The thallous compounds resulting from the epoxidation reactions described in the above-mentioned Kruse et al article and Kruse patent will be carboxylates and it is a feature of this invention that such thallous carboxylates can be converted to the thallic carboxylates with each so that the conversion products can be recycled to the epoxidation reaction.

The reaction medium for the conversion of monovalent thallium to trivalent thallium can be aqueous or non-aqueous. Non-aqueous media comprise organic solvents of various types as are well known to the art, including polar and non-polar solvents, but the polar solvents are particularly preferred. Typical polar organic solvents include the carboxylic acids such as acetic acid, ethers such as tetrahydrofuran and p-dioxane, dimethyl ethers of diethylene glycol and of triethylene glycol, tertiary alcohols such as t-butyl alcohol, aliphatic nitriles such as acetonitrile and propionitrile, amides such as dimethyl formamide and dimethyl acetamide, ketones such as acetone, methyl ethyl ketone and diethylketone, polar chlorinated hydrocarbons such as chloroform, as well as dimethyl sulfoxide, and the like, glycol ethers such as diethylene glycol, ethylene glycol dimethyl ether, ethylene glycol diethyl ether and diethylene glycol diethyl ether, glycol esters such as ethylene glycol diacetate, diethylene glycol diacetate, and the corresponding ethers and esters of propylene glycol, butylene glycol, and the like. Non-polar solvents include the hydrocarbons and chlorinated hydrocarbons such as carbontetrachloride. It will be understood that a solvent is preferably chosen which is not susceptible to oxidation under the particular conditions selected for the oxidation. Advantageiously an acid providing an anion to combine with all of the thallium (III) formed in present.

While an organic solvent can be used as the sole solvent component, a water-organic solvent mixture containing up to about 50 volume percent water, typically 5–10% water, can also be used, if desired. When water is present, and acids are absent, the trivalent thallium produced will normally be converted into the hydroxide which will precipitate and can be readily recovered and converted into any desired thallic salt in conventional manner, e.g., the hydroxide can be converted to a thallic salt by reaction with the appropriate acid.

If, however, an anion corresponding to the anion of the thallous compound is present, then the thallic compound will be obtained in the form of a salt containing that anion. On the other hand, other thallic salts can be formed by supplying the appropriate anion, e.g., by adding to the reaction mixture a mineral acid such as nitric acid, or a carboxylic acid such as benzoic acid, providing an anion different from the anion of the thallium salt charged. Thus, if the monovalent thallium is in the form of an acetate, then acetic acid is advantageously included in the reaction mixture so that all of the trivalent thallium will also be obtained in the form of the acetate. Sufficient acetic acid is, of course, present to provide the necessary molecular quantity. However, if a benzoate is desired, then benzoic acid is added to the reaction medium. The thallium (III) compound can thus be obtained in various forms as desired and, as mentioned, it can be in the same form as the thallium (I) compound supplied. The acids added to provide the anion for the thallium (III) compound can be any of the acids mentioned above in connection with the thallium (I) salt subjected to treatment, e.g., carboxylic acid such as alkyl, including cycloalkyl, and aryl carboxylic acids containing up to 20 carbon atoms and which, like the anions of the thallium (I) salts, can be substituted with non-reactive substituents such as halogen, alkoxy alkyl, and the like, or mineral acids, and the like.

Thus, monovalent thallium compounds can be readily converted to trivalent thallium compounds, and the reaction medium containing the trivalent thallium compound produced can be used directly or after suitable treatment, such as filtration to remove the catalyst, for epoxidation, or other reaction. The trivalent thallium compound can also be separated from the reaction medium by precipitation, evaporation of solvent, or the like, if desired.

The invention will be more fully understood by reference to the following examples of specific embodiments thereof but it will be understood that these examples are given for illustrative purposes only and are not intended as limitative of the invention. In the Examples, determinations of the thallium (III) product were carried out by means of conventional complexiometric analyses using standard ethylene nitrilo tetraacetic acid. The reaction mixture is analyzed in each case at the end of the indicated reaction period after cooling and depressurizing of the reaction vessel. Before analysis, the reaction mixture is filtered to separate the catalyst, and the filtered solids are washed with 1M acetic aicd. The combined filtrate and wash solution are then subjected to analysis.

EXAMPLE 1

A glass-lined pressure reactor is charged with a 0.6M solution of acetic acid in acetonitrile, 0.1 mol per liter of thallous acetate, 0.025 mol per liter of platinum, the platinum being supported on alumina and the support containing 5% by weight of the catalytic material, and 0.1 mol per liter of solution acetate. The reactor is pressurized with 500 psig of oxygen (25° C.) and then heated at 80° C. for 2 hours with continuous stirring. After cooling, depressurizing, filtering and washing, analysis of the combined filtrate and wash solution for thallic acetate showed a conversion of thallium (I) to thallium (III) of 67%.

EXAMPLE 2

Example 1 is repeated except that 0.1 mol per liter of cesium acetate is used instead of sodium acetate. The conversion of thallium (I) to thallium (III) is found to be 75%.

EXAMPLE 3

Example 1 is again repeated except that 0.3 mol per liter of rubidium acetate is used instead of sodium acetate. Analysis shows an 87% conversion of thallium (I) to thallium (III).

EXAMPLE 4

Again Example 1 is repeated except that 0.3 mol per liter of lithium acetate is used instead of sodium acetate. A 33% conversion of thallium (I) to thallium (III) is realized.

EXAMPLES 5-7

In these examples, the effect of varying amounts of potassium is shown. In three experiments Example 1 is repeated but the sodium acetate of Example 1 is replaced, respectively, by 0.05, 0.1 and 0.3 mol per liter of potassium acetate. The pertinent data are set forth in Table 1 below:

TABLE 1

| Example | Mol/l K Salt | Conversion to Thallium (III) % |
|---|---|---|
| 5 | 0.05 | 50 |
| 6 | 0.1 | 78 |
| 7 | 0.3 | 89 |

EXAMPLE 8

Example 1 is repeated but with the sodium acetate omitted from the charge, i.e., the reaction is conducted without the presence of a promoter in accordance with the invention. Analysis shows a 30% conversion of thallium (I) to thallium (III).

EXAMPLE 9

Example 1 is repeated but with 0.3 mol per liter of potassium hydroxide as promoter. Conversion of thallium (I) to thallium (III) is 78%.

The foregoing examples show that the metals of Group IA are promoters for the oxidation of thallium (I) to thallium (III) by means of molecular oxygen using Group VIII noble metal catalysts, and that the Group IA metals having atomic weights above 10 are particularly effective. On the other hand, the following example shows that the metal shown in Hirose et al. U.S. Pat. No. 3,399,956 to be the most effective catalyst for the process of that patent, i.e., copper, has no effect as a promoter for Group VIII noble metal catalysts in accordance with the present invention.

EXAMPLE 10

Example 1 is repeated except that the sodium acetate is replaced by an equal molar quantity of cupric acetate. No other change is made in the charge or procedure of Example 1. Analysis shows a 30% conversion of thallium (I) to thallium (III) corresponding to the non-promoted reaction described in Example 8.

The Hirose et al. patent also shows the use of alkali metals and alkaline earth metals as additives for the reaction system there disclosed, the alkaline earth metal illustrated (calcium) giving better results than the comparable salts of the alkali metals illustrated. The following example shows that in the process of the present invention, calcium has a negative effect upon the reaction.

EXAMPLE 11

Example 1 is again repeated exactly as described, except that the sodium acetate is replaced by 0.3 mol per liter of calcium acetate. Analysis shows only a 24% conversion of thallium (I) to thallium (III).

What is claimed is:

1. In a process for converting a thallium (I) compound to a thallium (III) compound in which the thallium (I) compound is reacted with molecular oxygen in the presence of a Group VIII noble metal, the improvement which comprises effecting said reaction in the presence of a promoter comprising a Group IA metal compound.

2. A process as defined in claim 1 wherein the promoter is employed in an amount of from 0.01 to 50 moles of promoter per mole of thallium (I) compound.

3. A process as defined in claim 1 wherein the promoter is employed in an amount of from 0.1 to 10 moles of promoter per mole of thallium (I) compound.

4. A process as defined in claim 1 wherein the thallium (I) compound comprises a salt derived from an alkyl, cycloalkyl or aryl carboxylic acid having up to twenty carbon atoms.

5. A process as defined in claim 4 wherein said reaction is effected in the presence of a carboxylic acid.

6. A process as defined in claim 1, wherein the metal has an atomic weight greater than 10.

7. A process as defined in claim 1, wherein the metal is sodium, potassium, cesium or rubidium.

8. A process as defined in claim 1, wherein the reaction is carried out in a liquid medium.

9. A process as defined in claim 1, wherein the Group VIII noble metal is platinum or palladium.

10. A process as defined in claim 1, wherein the reaction is carried out under an oxygen partial pressure of 20 to 10,000 psi.

11. A process as defined in claim 1, wherein the thallium (I) compound is a thallium (I) carboxylate.

* * * * *